US00PP26055P3

(12) United States Plant Patent
Bradford et al.

(10) Patent No.: US PP26,055 P3
(45) Date of Patent: Nov. 10, 2015

(54) INTERSPECIFIC TREE NAMED 'PLUMSWEET XVI'

(50) Latin Name: ***Prunus* sp.**
Varietal Denomination: Plumsweet XVI

(71) Applicants: Lowell Glen Bradford, Le Grand, CA (US); Jon Michael Quisenberry, Merced, CA (US)

(72) Inventors: Lowell Glen Bradford, Le Grand, CA (US); Jon Michael Quisenberry, Merced, CA (US)

( * ) Notice: Subject to any disclaimer, the term of this patent is extended or adjusted under 35 U.S.C. 154(b) by 164 days.

(21) Appl. No.: 13/998,854

(22) Filed: Dec. 16, 2013

(65) Prior Publication Data

US 2015/0173269 P1 Jun. 18, 2015

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP14,196 P2 9/2003 Bradford
PP23,686 P2 6/2013 Bradford

*Primary Examiner* — Susan McCormick Ewoldt

(57) ABSTRACT

The present invention relates to an interspecific tree and more particularly to a new and distinct variety broadly characterized by a medium size, vigorous, hardy, and productive tree. Being self-unfruitful, the present variety requires cross pollination from an apricot, interspecific, or plum that blooms during the mid to late season. The present variety produces a heavy bloom with an abundant amount of pollen to entice good bee activity to facilitate pollination. The fruit matures under the ecological conditions described during July, with first picking on Jul. 8, 2013, and can hang on the tree for up to two weeks. The fruit is uniformly large in size, a green and red two-tone in skin color, full red in flesh color, clingstone in type, oblate in shape, firm in texture, juicy, and very good in flavor.

1 Drawing Sheet

Botanical classification: *Prunus* sp.
Varietal denomination: 'PLUMSWEET XVI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of interspecific tree which has been denominated varietally as 'Plumsweet XVI'.

During a typical blooming season we isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2004 one such house containing 'Plumsweettwo' (U.S. Plant Pat. No. 14,196) plum tree was crossed by us in this manner. To pollinate this plum, we selected bouquets from several sources of apricot and interspecific hybrid trees without keeping specific written details. Upon reaching maturity the fruit from this plum tree was harvested and the seeds were removed, cracked, stratified and germinated as a group with the label "H15". They were grown as seedlings on their own root in our greenhouse and upon reaching dormancy transplanted to a cultivated area of our experimental orchard located near Le Grand, Calif. in Merced County (San Joaquin Valley). During the summer of 2008 the claimed variety was selected by us as a single plant from the group of seedlings described above. Subsequent to origination of the present variety of interspecific tree, we asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Plumsweettwo' plum (U.S. Plant Pat. No. 14,196), by being self-unfruitful and by producing fruit that is full red in flesh color, firm in texture, and very good in flavor, but is distinguished therefrom by producing fruit that is larger in size, that is a red and green two-tone in skin color instead of full purple, and that matures about two weeks earlier.

The present variety is most similar to 'Plumsweet XIV' (U.S. Plant Pat. No. 23,686) interspecific tree, by being self-unfruitful and by producing fruit that is a green and red two-tone in skin color, full red in flesh color, firm in texture, juicy, and sweet in flavor, but is distinguished therefrom by producing fruit that is much more oblate in shape, that is larger in size, and that is less prone to skin cracking.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the mid to late season. The present variety produces a heavy bloom with an abundant amount of pollen to entice good bee activity to facilitate pollination. The fruit matures under the ecological conditions described during July, with first picking on Jul. 8, 2013, and can hang on the tree for up to two weeks. The fruit is uniformly large in size, a green and red two-tone in skin color, full red in flesh color, clingstone in type, oblate in shape, firm in texture, juicy, and very good in flavor.

DRAWING

The accompanying photograph consists of four whole fruits positioned to display the characteristics of the skin color and form, a half fruit divided to reveal the flesh and stone, a seed, a tip shoot growth, typical leaves, and an inset depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 15, 2013, on the original tree during its ninth growing season. The flower and bud descriptions were developed during the previous blooming season. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

PARENTAGE

Seed parent: 'Plumsweettwo' plum (U.S. Plant Pat. No. 14,196).

Pollen parent: Unknown.

TREE

Size: Medium, reaching and maintaining a height of 9' [2.74 m.] and a spread of 7' [2.13 m.] after nine growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming apricot, interspecific, or plum, such as 'Blackred V' (U.S. Plant Pat. No. 19,576).

Bearing: Regular bearer, with no crop failures observed.

Trunk:

- *Size*.—Medium, reaching a maximum diameter of 4" [102 mm.] after the ninth growing season.
- *Texture*.—Medium shaggy.
- *Bark color*.—A Grayish brown [61. gy.Br] and Dark grayish brown [62. d.gy.Br] variegation with Brownish orange [54. brO] crevices present.
- *Lenticels*.—Approximate Number Per Square Inch: 10. Color: Moderate yellowish brown [77. m.yBr]. Average Size: ⅛" [3.2 mm.]. Shape: Eye-shaped, elongated.

Branches:

- *Size*.—Diameter of limb is 2" [50.8 mm.] measured 12" above the crotch, 1" [25.4 mm.] measured 12" above the first fork.
- *Texture*.—Smooth on first and second year wood, increasing roughness with age.
- *Color*.—1st Year Wood Topside: Grayish red [19. gy.R]. 1st Year Wood Underside: Brilliant yellow green [116. brill.YG]. Older Wood: A Grayish brown [61. gy.Br] and Brownish gray [64. brGy] variegation with Light yellowish brown [76. l.yBr] crevices present.
- *Lenticels*.—Number Per Square Inch: About 60 on second year wood. Color: Light yellowish brown [76. l.yBr]. Average Size: 1/64" [0.4 mm.]. Shape: Elongated, rectangular.

Leaves:

- *Size*.—Medium. Average Length: 3½" [88.9 mm.]. Average Width: 1 9/16" [39.7 mm.].
- *Arrangement*.—Alternate.
- *Thickness*.—Medium.
- *Form*.—Elliptical.
- *Apex*.—Acuminate.
- *Base*.—Acute with an average angle base angle of 70 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Petiole*.—Average Length: 7/16" [11.1 mm.]. Average Thickness: 1/16" [1.6 mm.]. Color: Light yellow green [119. l.YG].
- *Stipules*.—Number: 2 per leaf, up to 6 per growing tip. Average Length: ¼" [6.4 mm.]. Color: Light yellow green [119. l.YG] becoming Moderate olive green [125. m.OlG] with age.
- *Glands*.—Number: Mostly 2 per leaf. Position: A slightly alternate, positioned at the intersection of the petiole and base of leaf blade. Size: Small. Form: Globose. Color: Deep yellow green [118. deep YG] becoming Moderate olive green [125. m.OlG] in the center with age. Leaf buds: Pointed, medium.

Flower buds:

- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, about thirty stamens, five sepals and petal locations alternately positioned.

- *Average flower diameter*.—1" [25.4 mm.].
- *Number of petals*.—Five, no double blossoms observed.
- *Petal shape*.—Oval to circular.

*Petal margin*.—Entire, smooth to slightly wavy.
*Average petal diameter*.—½" [12.7 mm.].
*Average petal length*.—9/16" [14.3 mm.].
*Petal apex*.—Rounded.
*Petal base*.—Obtuse.
*Petal color*.—White [263. White] on both sides.
*Anther color*.—Vivid yellow [82. v.Y].
*Stigma color*.—Light yellow [86. l.Y].
*Sepal color*.—A Moderate yellow green [120. m.YG] and Light reddish brown [42. l.rBr] two-tone on the outer surface.
*Sepal length*.—7/32" [5.6 mm.].
*Sepal width*.—5/32" [4.0 mm.].
*Sepal apex*.—Rounded to elliptical to match the width and length.
*Sepal margin*.—Fairly smooth with slight serrations toward the apex.
*Average pistil length*.—⅝" [15.9 mm.].
*Average stamen length*.—½" [12.7 mm.].
*Fragrance*.—Moderate.
*Bloom density*.—Heavy.
*Number per cluster*.—2 to 10, average 5.
*Pollen production*.—Abundant, strong enticement to bees.
*Blooming period*.—Mid to late, three days after 'September Yummy' plum (U.S. Plant Pat. No. 14,220).
*Onset of bloom*.—One percent on Mar. 1, 2013.
*Date of full bloom*.—Mar. 10, 2013.
*Duration of bloom*.—One to two weeks, dependent on ambient temperature.

FRUIT

Maturity when described: Firm ripe, Jul. 15, 2013.
Date of first picking: Jul. 8, 2013.
Date of last picking: Jul. 22, 2013.
Size: Uniform, large.
*Average diameter axially*.—2¼" [57.2 mm.].
*Average diameter across cheek plane*.—2¾" [69.9 mm.].
*Average diameter across suture plane*.—2¾" [69.9 mm.].
*Typical weight*.—5.4 ounces [153 grams].
Form: Uniform, oblate, symmetrical.
*Longitudinal section form*.—Oblate.
*Transverse section through diameter*.—Round.
Suture: An inconspicuous Grayish red [19. gy.R] line located in a very shallow groove extending from the base to the apex.
Ventral surface: Rounded, slightly lipped toward the base.
Lips: Equal.
Cavity: Flaring, circular, suture showing on one side.
*Depth*.—1⅛" [28.6 mm.].
*Breadth*.—7/16" [11.1 mm.].
Base: Truncate, slightly cordate if viewed parallel to the suture.
Apex: Truncate.
Pistil point: An inconspicuous Grayish yellowish brown [80. gy.yBr] dot.
Stem: Medium.
*Average length*.—7/16" [11.1 mm.].
*Average width*.—3/32" [2.4 mm.].
Skin:
*Thickness*.—Medium.
*Surface*.—Smooth.
*Tenacity*.—Tenacious to the flesh.
*Astringency*.—Slight.
*Tendency to crack*.—Slight if in contact with the limb.
*Color*.—A Deep red [13. deep R] and Moderate yellow green [120. m.YG] two-tone with some Dark red [16. d.R] mottling and streaking.
*Bloom*.—Abundant.
Flesh:
*Color*.—A Very deep red [14. v.deep R] toward the skin and stone, with Strong red [12. s.R] in the middle.
*Surface of pit cavity*.—Covered with Light yellowish pink [28. l.yPk] broken fibers when twisted away from stone.
*Amygdalin*.—Moderate.
*Juice*.—Abundant, rich.
*Texture*.—Firm, crisp, meaty.
*Fibers*.—Abundant, fine.
*Ripens*.—Slightly earlier toward the apex.
*Flavor*.—A tasty blend of acid and sugar, typically 18 brix.
*Aroma*.—Very slight.
*Eating quality*.—Very good.

STONE

Type: Clingstone.
Form: Oval.
Hilum: Narrow.
Base: Slightly cordate.
Apex: Acuminate.
Sides: Unequal.
Surface: Irregularly furrowed near apex.
External color of stone: Strong yellowish brown [74. s.yBr].
Pit wall color when cracked: Light yellowish brown [76. l.yBr].
Cavity surface color: Dark orange yellow [72. d.OY].
Average pit wall thickness: 1/16" [1.6 mm.].
Average width: ⅝" [15.9 mm.].
Average length: 15/16" [23.8 mm.].
Average breadth: 5/16" [7.9 mm.].
Tendency to split: None observed.
Kernel:
*Form*.—Oval.
*Skin color*.—Pale orange yellow [73. p.OY] when first removed.
*Pellicle color*.—Moderate orange yellow [71. m.OY].
*Vein color*.—Light orange yellow [70. l.OY].
*Taste*.—Bitter.
*Viable*.—Yes.
*Average width*.—⅜" [9.5 mm.].
*Average length*.—½" [12.7 mm.].
*Amygdalin*.—Moderate.

USE

Market: Fresh market and long distance shipping.
Keeping quality: Good, fruit quality observed to remain in good condition after 30 days in standard cold room at 36° Fahrenheit [2° Celsius].

Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of interspecific *Prunus* sp. tree, substantially as illustrated and described, that is most similar to 'Plumsweet XIV' (U.S. Plant Pat. No. 23,686) interspecific tree, by being self-unfruitful and by producing fruit that is a green and red two-tone in skin color, full red in flesh color, firm in texture, juicy, and sweet in flavor, but is distinguished therefrom by producing fruit that is much more oblate in shape, that is larger in size, and that is less prone to skin cracking.

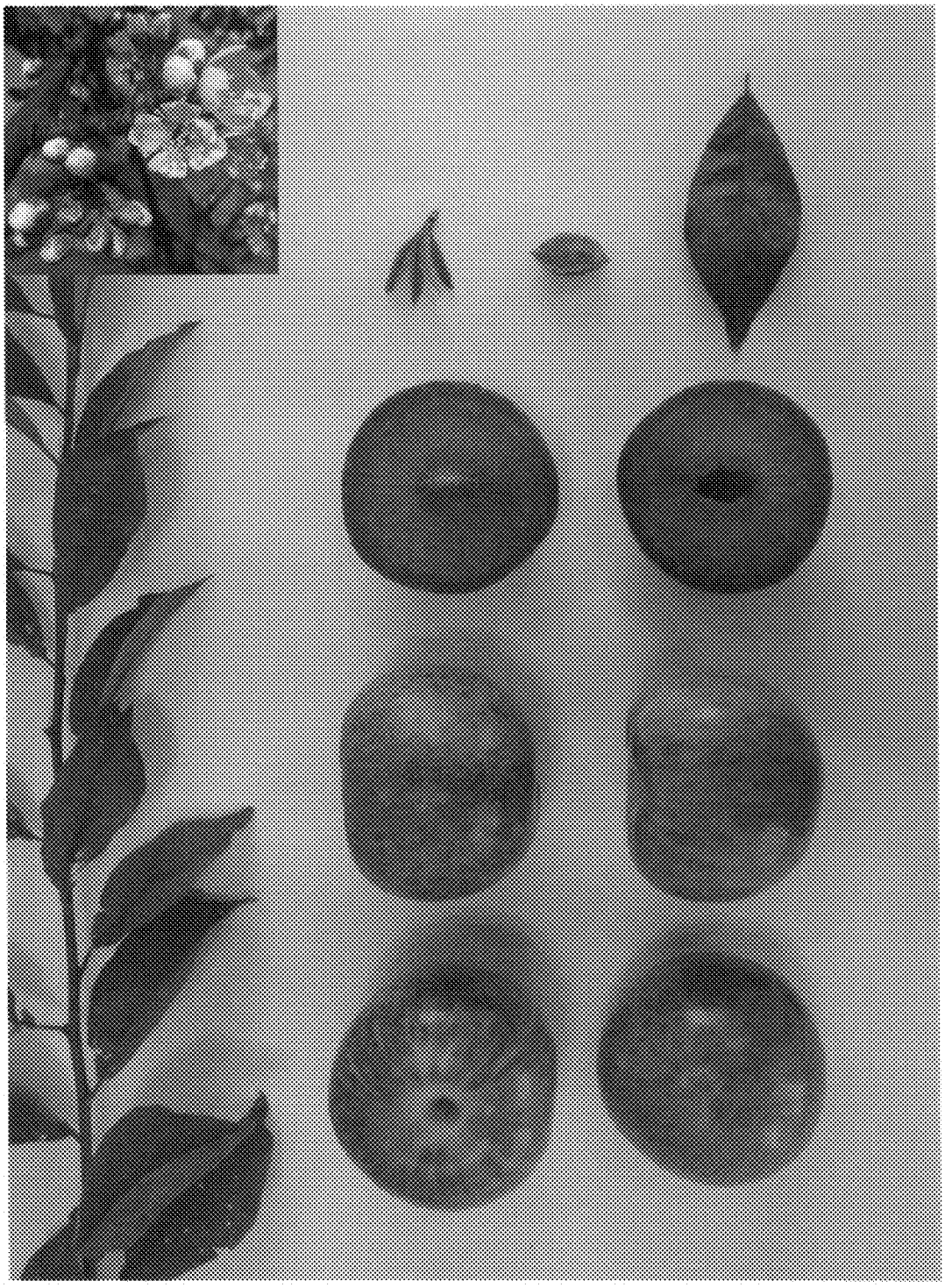

* * * * *